United States Patent
Kobayashi

(10) Patent No.: US 9,545,629 B2
(45) Date of Patent: Jan. 17, 2017

(54) MICRO FLOW-CHANNEL CHIP, METHOD FOR MANUFACTURING THE SAME, AND DEVICE FOR ANALYSIS

(71) Applicant: CANON KABUSHIKI KAISHA, Tokyo (JP)

(72) Inventor: Daigo Kobayashi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 139 days.

(21) Appl. No.: 14/509,206

(22) Filed: Oct. 8, 2014

(65) Prior Publication Data

US 2015/0118739 A1    Apr. 30, 2015

(30) Foreign Application Priority Data

Oct. 24, 2013   (JP) ................. 2013-221096

(51) Int. Cl.
*B01L 3/00* (2006.01)
*B01L 7/00* (2006.01)
*G01N 15/14* (2006.01)

(52) U.S. Cl.
CPC .......... *B01L 3/5027* (2013.01); *B01L 3/50273* (2013.01); *B01L 3/502707* (2013.01); *B01L 2200/027* (2013.01); *B01L 2200/0684* (2013.01); *B01L 2200/12* (2013.01); *B01L 2300/0816* (2013.01); *B01L 2300/0819* (2013.01); *B01L 2300/0851* (2013.01); *B01L 2300/0867* (2013.01); *B01L 2300/0887* (2013.01); *B01L 2300/12* (2013.01); *B01L 2300/1805* (2013.01); *B01L 2400/0487* (2013.01); *G01N 15/1484* (2013.01)

(58) Field of Classification Search
CPC ................. B01L 2200/027; B01L 2200/0684; B01L 2200/12; B01L 2300/0816; B01L 2300/0819; B01L 2300/0851; B01L 2300/0867; B01L 2300/0887; B01L 2300/12; B01L 2300/1805; B01L 2400/0487; B01L 3/50
See application file for complete search history.

(56) References Cited

U.S. PATENT DOCUMENTS

| | | | |
|---|---|---|---|
| 2009/0232708 A1* | 9/2009 | Yokogawa | B01L 3/5027 422/400 |
| 2011/0008223 A1* | 1/2011 | Tsao | B01L 3/502715 422/502 |
| 2012/0058519 A1 | 3/2012 | Knight et al. | |
| 2014/0044610 A1* | 2/2014 | Miyoshi | B01L 3/502707 422/502 |
| 2014/0186214 A1* | 7/2014 | Momose | B01L 3/502753 422/68.1 |

* cited by examiner

*Primary Examiner* — Jennifer Wecker
(74) *Attorney, Agent, or Firm* — Fitzpatrick, Cella, Harper & Scinto

(57) ABSTRACT

The present invention provides a micro flow-channel chip formed of two or more parts, wherein a first part has a through hole that forms a flow-channel connection portion, a second part has a projecting portion, the projecting portion of the second part is inserted into the through hole of the first part, thereby a volume of the flow-channel connection portion is reduced, and furthermore, both of the first part and the second part are molded with a die.

15 Claims, 4 Drawing Sheets

MICRO FLOW-CHANNEL CHIP, METHOD FOR MANUFACTURING THE SAME, AND DEVICE FOR ANALYSIS

BACKGROUND OF THE INVENTION

Field of the Invention

The present invention relates to a micro flow-channel chip, a method for manufacturing the same, and a device for analysis.

Description of the Related Art

In recent years, a technology is proposed which enables an inspection with a unit of several µL to nL, by forming a fine reaction field by using a lithographic process technology or a thick-film process technology. A technology using such a fine reaction field is referred to as µ-TAS (Micro Total Analysis system).

The µ-TAS is applied to: a region of a genetic test, a chromosomal test and a cytoscopy of a human, and the like; a biotechnology; a test of a trace amount of a substance in an environment; an investigation on a farming environment of an agricultural product and the like; a genetic test for an agricultural product; and the like. In µ-TAS, in many cases, a flow channel with a micro size (micro flow-channel and micro channel) is used, which is formed on a substrate. Such a substrate is referred to as a chip, a microchip, a micro flow-channel chip or the like.

U.S. Patent Publication No. 2012/0058519 discloses a micro flow-channel chip (Interface chip) having a plurality of specimen introduction portions, and a second micro flow-channel chip (reaction chip) in which a specimen delivered from the micro flow-channel chip is analyzed. In addition, a device is disclosed in which these micro flow-channel chips are combined with each other. This device introduces a specimen into the first micro flow-channel chip, and analyzes the introduced specimen therein, while changing a plurality of trace specimens from one to another. The change described here means that two or more kinds of specimens are repeatedly and continuously introduced into the microchip.

In the device described in U.S. Patent Publication No. 2012/0058519, which analyzes specimens while changing trace specimens from one to another, a cross-sectional area of the flow channel increases in a connection portion between a flow channel and a flow channel or between a flow channel and an introduction port and the like, and a place is formed in which the specimen is detained. There has been a problem that the specimen results in being mixed with the previous specimen when the specimen liquid is continuously sent, in the place in which the specimen is detained. Accordingly, a first subject of the present invention is to provide a micro flow-channel chip in which the previous specimen resists remaining in the chip when the specimen is changed.

A second subject of the present invention is to provide a micro flow-channel chip which can be manufactured by die molding. A portion of the micro flow-channel chip, in particular, out of the whole of the micro flow-channel device, is disposed in many cases, and it is important to reduce a manufacture cost of the chip. In order to reduce the cost, the micro flow-channel chip is desirably manufactured by die molding.

SUMMARY OF THE INVENTION

The present invention is a micro flow-channel chip formed of two or more parts, wherein a first part has a through hole that forms a flow-channel connection portion, a second part has a projecting portion, and the projecting portion of the second part is inserted into the through hole of the first part.

Further features of the present invention will become apparent from the following description of exemplary embodiments with reference to the attached drawings.

BRIEF DESCRIPTION OF THE DRAWINGS

FIG. 1A is a view illustrating the micro flow-channel chip; FIG. 1B is a view illustrating an example of a first part; FIG. 1C is a view illustrating an example of a second part; and FIG. 1D is an enlarged view of a through hole of the first part. The through hole of the first part forms a flow-channel connection portion of the micro flow-channel chip. FIG. 1E is an enlarged view of a projecting portion of a second part; and FIG. 1F is a view illustrating that a volume of the flow-channel connection portion which is formed by the through hole portion is reduced by the projecting portion.

FIG. 2A is a top plan view of the device for analysis; FIG. 2B is a view illustrating a flow of a specimen in the device for analysis; and FIG. 2C is an enlarged view of a second micro flow-channel chip.

FIG. 3A is a view illustrating a first form in which a first specimen is guided to the micro flow-channel chip; FIG. 3B is a view illustrating a second form in which the first specimen is guided to a second micro flow-channel chip from the micro flow-channel chip; FIG. 3C is a view illustrating a third form in which a second specimen is guided to the micro flow-channel chip; FIG. 3D is a view illustrating a fourth form in which the second specimen is guided to the second micro flow-channel chip from the micro flow-channel chip; and FIG. 3E is a view illustrating a state in which several kinds of specimens have been guided to the device for analysis.

DESCRIPTION OF THE EMBODIMENTS

Preferred embodiments of the present invention will now be described in detail in accordance with the accompanying drawings.

A first embodiment of the present invention is a micro flow-channel chip formed of two or more parts, in which the first part has a through hole that forms a flow-channel connection portion, and the second part has a projecting portion, wherein the projecting portion of the second part is inserted into the through hole of the first part. Both of the first part and the second part can be molded with a die. In addition, the flow-channel connection portion can include being connected with the micro flow-channel. The first part can include a cycloolefin polymer, polymethyl methacrylate, polycarbonate, a methyl methacrylate styrene copolymer or polystyrene; and the second part can include a cycloolefin polymer, polymethyl methacrylate, polycarbonate, a methyl methacrylate styrene copolymer or polystyrene. The shape of the projecting portion can include a circular truncated cone shape, a conical shape, a polygonal pyramid shape and a polygonal truncated pyramid shape.

A second embodiment of the present invention is a device for analysis, which includes being provided with the micro flow-channel chip, or a micro flow-channel device which is formed of a micro flow-channel chip and a micro flow-channel chip made from glass.

A third embodiment of the present invention is a method for manufacturing a micro flow-channel chip which is formed of two or more parts, including: manufacturing a first part having a through hole with die molding, by using a first die; manufacturing a second part having a projecting portion with die molding, by using a second die; and joining the first part with the second part, wherein the projecting portion is inserted into the through hole to form a flow-channel connection portion. The parts can be joined with each other by thermo compression bonding, bonding by an adhesive, threading or sandwiching. In addition, the first part and the second part can be manufactured by die-molding a resin with the use of the first die or the second die, and the above described resin can be a cycloolefin polymer, polymethyl methacrylate, polycarbonate, a methyl methacrylate styrene copolymer or polystyrene.

The micro flow-channel chip is a substrate which has a micro flow-channel, specifically, a flow channel with a diameter of 1 mm or less, and can include, for instance, a DNA chip, a Lab on a Chip, a microarray and a protein chip.

The part means a component which forms the micro flow-channel. The micro flow-channel chip is formed of two or more parts, and the first part and the second part are manufactured by die molding. When there exist other parts, the other parts may be molded with a die or may be manufactured by another method.

Figure 4A:
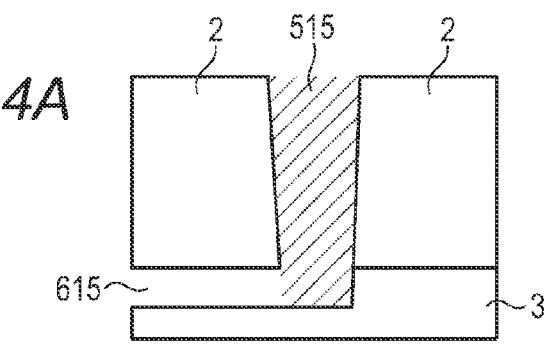
FIG. 4A is a view of a flow-channel connection portion of a conventional micro flow-channel chip.
Figure 4B:
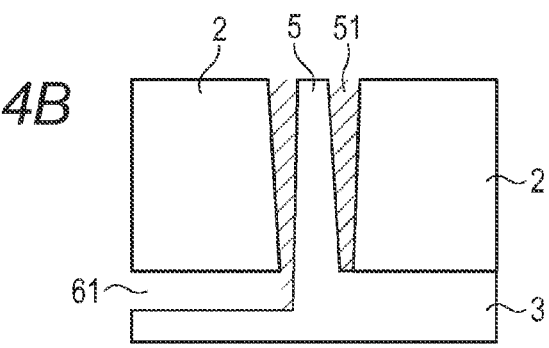
FIG. 4B is a view of a flow-channel connection portion of a micro flow-channel chip of the present invention.
Figure 4C:
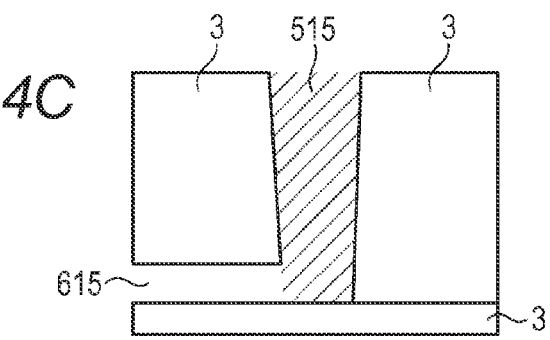
FIG. 4C is a view of the flow-channel connection portion of the conventional micro flow-channel chip.
Figure 4D:
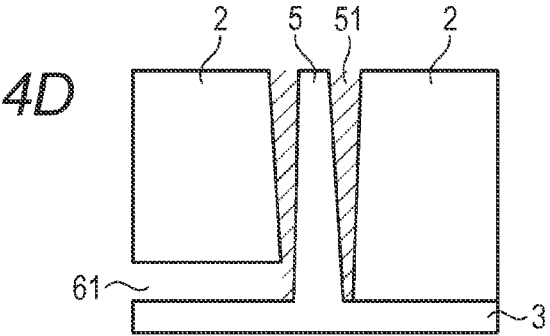
FIG. 4D is a view of the flow-channel connection portion of the micro flow-channel chip of the present invention.

The flow-channel connection portion means an introducing portion or a connecting portion for introducing a sample into the micro flow-channel or for introducing the sample into the micro flow-channel from the micro flow-channel, and a flow-channel connection portion 515 of a conventional micro flow-channel is shown in by diagonal lines in FIGS. 4A and 4C. The flow-channel connection portion 515 is formed of the through hole which is formed in the first part. As for the flow-channel connection portion 51 of the present invention, as are illustrated in FIGS. 4B and 4D, the volume of the flow-channel connection portion 51 is reduced by the projecting portion which is formed on the second part. Incidentally, FIGS. 4A and 4B illustrate examples in which a flow channel 61 or 615 is formed by the shape of the second part 3; and FIGS. 4C and 4D illustrate examples in which the flow channel 61 is formed by the shape of the first part 2.

The die molding is a method for working resin, plastic, metal and the like, and means a manufacturing method of filling a die with the material and molding the filled material. A base material for the micro flow-channel chip of the present invention is not limited in particular, as long as the base material is molded with a die. Materials to be used for the first part can include resins such as COP (cycloolefin polymer), PMMA (polymethyl methacrylate), PC (polycarbonate), MS (methyl methacrylate styrene copolymer) and PS (polystyrene). Materials to be used for the second part can include resins such as COP (cycloolefin polymer), PMMA (polymethyl methacrylate), PC (polycarbonate), MS (methyl methacrylate styrene copolymer) and PS (polystyrene). The materials of the first part and the second part can be the same, but need not to be always the same.

Figure 1A:
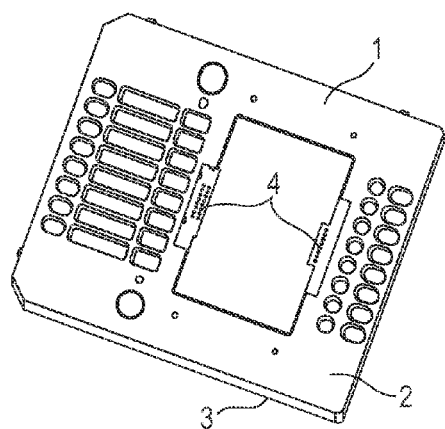
FIGS. 1A, 1B, 1C, 1D, 1E and 1F are views illustrating a micro flow-channel chip according to embodiments and exemplary embodiments of the present invention.
Figure 1B:
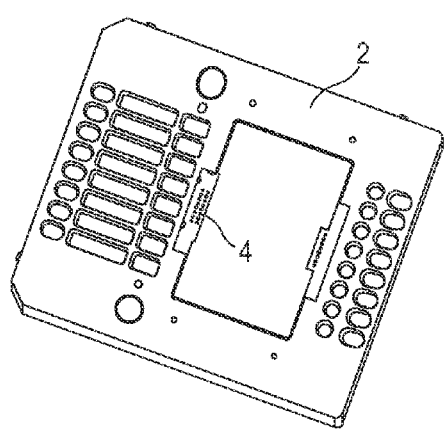
Figure 1C:
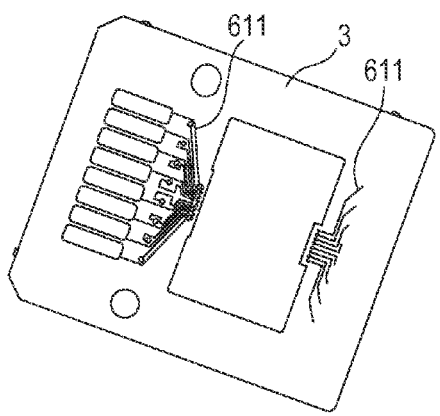
Figure 1D:
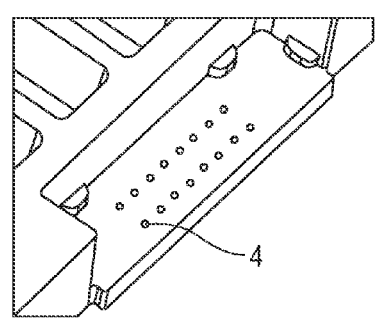
Figure 1E:
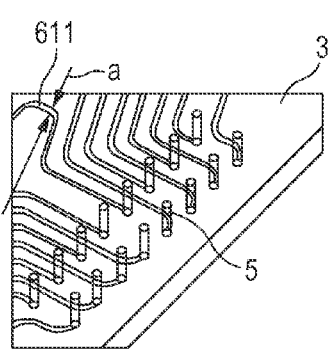
Figure 1F:
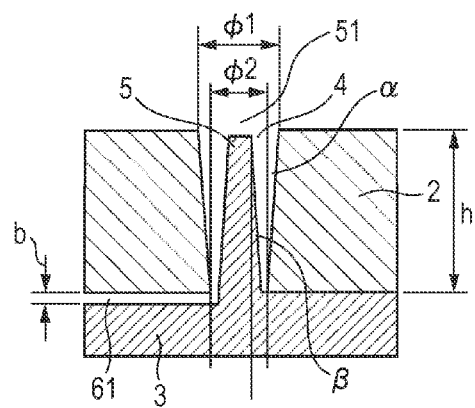

FIGS. 1A to 1F illustrate the micro flow-channel chip in the present invention. FIG. 1A is a view illustrating an example of the micro flow-channel chip 1 in the present invention (in order to distinguish micro flow-channel chip 1 from second micro flow-channel chip, example of micro flow-channel chip of present invention is hereafter referred to occasionally as "first micro flow-channel chip" or "first chip"). FIG. 1B is a view illustrating an example of a first part 2 which forms the micro flow-channel chip, and the micro flow-channel chip has a through hole 4. In the example of the present figure, the through hole 4 is connected to the micro flow-channel of a not-shown second micro flow-channel chip. FIG. 1C is a view illustrating an example of a second part 3 which forms the micro flow-channel chip. The second part 3 has a projecting portion 5, and a groove 611 for forming a flow channel 61. FIG. 1D is an enlarged view of the through hole of the first part 2. FIG. 1E is an enlarged view of the projecting portion 5 of the second part 3. FIG. 1F illustrates a cross-sectional view in which the first part 2 and the second part 3 are bonded to each other. FIG. 1F illustrates a cross-sectional view in which the projecting portion 5 is inserted into the through hole 4. In the figure, a bore diameter $\phi 1$ in the portion is shown which is connected to the second micro flow-channel chip (for instance, chip made from glass), and a height h of the hole is shown. In addition, in the figure, a width a of the groove 611 is shown, and a depth b of the flow channel 61 is shown.

When the first part 2 is manufactured, a die having such a shape that the shape of the part is inverted is manufactured, and the first part 2 is manufactured with the die molding. In addition, when the first part 2 is manufactured by die molding, the through hole 4 can have an extraction gradient so that the first part 2 is not deformed when being released from the die. In other words, an inner wall which forms the through hole 4 can be inclined. The extraction gradient (angle of inclination of inner wall) $\alpha$ can be 1 degree or more and 5 degrees or less, and can be set, for instance, at 2 degrees. If the angle is smaller than 1 degree, the first part 2 results in occasionally being deformed when being released from the die. In addition, if the angle is larger than 5 degrees, a diameter difference of the through hole between a diameter $\phi 1$ of the hole in a first face of the first part and a diameter $\phi 2$ of the hole in a second face of the first part results in being large, and stagnation results in occasionally occurring in a flow of the specimen. The cross-sectional area (cross-sectional area perpendicular to longitudinal direction of hole) of the through hole 4 can be as equal as possible to the cross-sectional area (cross-sectional area perpendicular to longitudinal direction of flow channel) of the flow channel 61. If the difference of the cross-sectional area is large, stagnation results in occasionally occurring in the flow. In addition, the cross-sectional areas of the through hole 4 and the flow channel 61 can be as small as possible. If the cross-sectional area is large, the amount of the specimen for being passed in the flow channel 61 and the through hole 4 needs to be that much larger.

As for the size of the through hole 4, the diameter $\phi 1$ of the hole in the first face of the first part can be $\phi 0.35$ mm or more and $\phi 0.45$ mm or less.

The first part 2 in which the through hole 4 has been formed can be manufactured by being molded, for instance, with a die having a pin formed therein. Accordingly, the diameter in a root portion of the pin for molding the through hole 4 can be $\phi 0.35$ mm or more and $\phi 0.45$ mm or less. The hole having a diameter smaller than φ0.35 mm results in being molded by a pin having a diameter smaller than φ0.35 mm. The pin having a diameter smaller than φ0.35 mm is very brittle, and when the through hole 4 is molded with the die, the pin is occasionally damaged by a pressure of a resin in the molding and/or a resistance occurring when the resin is released from the die.

The flow channel 61 can be manufactured by forming the groove 611 on the surface of the second part 3. As for the shape of the flow channel 61, the cross-sectional shape (shape of cross section perpendicular to longitudinal direction of flow channel) may be a semicircle or a polygon such as a triangle and a quadrangle. The quadrangular flow channel 6 can be formed by the groove 611 having a quadrangular shape, for instance, of which the width a is 0.10 mm and the depth b is 0.05 mm. In addition, on the second part, after the second part has been bonded to the first part, the projecting portion 5 is formed which fits in the inner part of the through hole 4. The micro flow-channel chip shows the effect of the present invention even though the projecting portion 5 has any shape as long as the projecting portion fits in the inner part of the through hole 4.

In the present embodiment, an example is illustrated in which the projecting portion 5 has a circular truncated cone shape of which the diameter of the root portion is φ0.1 mm or more and φ0.35 mm or less. The projecting portion 5 can have an extraction gradient. Specifically, the side face of the projecting portion 5 can be formed of a slope which is inclined so that the transverse section becomes thicker as the position moves to the root. The extraction gradient (angle of inclination of slope of circular truncated cone shape) β can be 1 degree or more and 5 degrees or less, and can be set, for instance, at 2 degrees. If the angle is smaller than 1 degree, the first part 2 results in occasionally being deformed when being released from the die. In addition, if the angle is larger than 5 degrees, a diameter difference of the through hole between a diameter φ1 of the hole in a first face of the first part and a diameter φ2 of the hole in a second face of the first part results in being large, and stagnation results in occasionally occurring in a flow of the specimen. In addition, a difference between the height of the projecting portion 5 and a height h of the through hole 4 can be small. In the present embodiment, the example has been described in which the projecting portion has the circular truncated cone shape, but may have another shape. For instance, even though the projecting portion has a conical shape, a polygonal pyramid shape, a polygonal truncated pyramid shape or the like, the same effect can be obtained. However, it is difficult to manufacture projecting portions having a columnar shape and a polygonal column shape by die molding.

When the second part is manufactured, a die having such a shape that the shape of the part is inverted is manufactured, and the second part can be manufactured with the die molding. Specifically, such a projecting shape that the shape of the groove 611 that forms the flow channel 61 is inverted is manufactured in the die, and at the same time, such a hole shape that the shape of the projecting portion 5 is inverted is manufactured in the die. Then, the die is filled with a resin, and the second part in which the groove 611 and the projecting portion 5 are formed is manufactured with molding.

After that, the first part 2 and the second part are bonded to each other, for instance, with an ultraviolet-curable type adhesive, and thereby the micro flow-channel chip 1 according to the present invention is obtained. The obtained micro flow-channel chip 1 has the projecting portion 5 provided in the inner part of the through hole 4, thereby can reduce a volume of the flow-channel connection portion 51, and can form the flow-channel connection portion 51 which has the cross-sectional area that is approximately equal to that of the flow channel 61. In addition, the flow channel 61 is formed by a space which is formed between the bottom face of the first part 2 and the groove 611 of the second part 3, after the parts have been bonded with each other. Thereby, the micro flow-channel chip can reduce the stagnation in the flow of the specimen, can have a configuration in which the previous specimen resists remaining in the chip when the specimen is changed, can reduce the amount of the specimen to be used, and can perform an efficient analysis.

A method of joining the parts with each other is not limited, and can adopt any method, for instance, such as thermo compression bonding, bonding by an adhesive or the like, threading and sandwiching.

The micro flow-channel chip in the present invention has the projecting portion 5 provided in the inner part of the through hole 4 existing in the first part 2, thereby reduces the volumetric capacity of the flow-channel connection portion 51 of the micro flow-channel thereon, can have the configuration in which the previous specimen resists remaining in the chip when the specimen is changed, and can reduce the amount of the specimen to be used. Accordingly, a time period can be reduced which is spent before the next introduced specimen lets the remaining previous specimen flow out, and the efficient analysis can be performed.

In the modes for carrying out the present invention, a configuration will be described below in which two kinds of parts of the first part 2 and the second part are joined with each other to provide the micro flow-channel chip 1, but the present invention is not necessarily limited to this configuration. In order to lower the molding difficulty in the die molding, for instance, it is acceptable to further divide each of the first part and the second part and obtain the micro flow-channel chip 1 from three or more kinds of parts, or to include another part as a part other than the first part and the second part. Another part can include any component, and can include a second flow-channel chip, packing, a part for an introduction portion, a part for detection, and a pump, as examples.

In addition, in the example of FIGS. 1A to 1F, the groove 611 which forms the flow channel 61 is formed on the second part. However, the groove 611 which forms the flow channel 61 may be formed on the first part, as is illustrated in the example of FIG. 4D (FIGS. 4C and 4D).

The micro flow-channel chip of the present invention can be used for sending a specimen liquid to a second micro flow-channel chip in which the specimen is analyzed. In the following embodiment, an example is shown in which a micro flow-channel chip made from glass is provided as the second micro flow-channel chip. Incidentally, the second micro flow-channel chip may be or may not be molded with a die, but if being a chip made from glass, the chip is superior in heat resistance. Accordingly, the chip made from glass is desirably used in the case where the introduced specimen is amplified by PCR or the like.

Figure 2A:
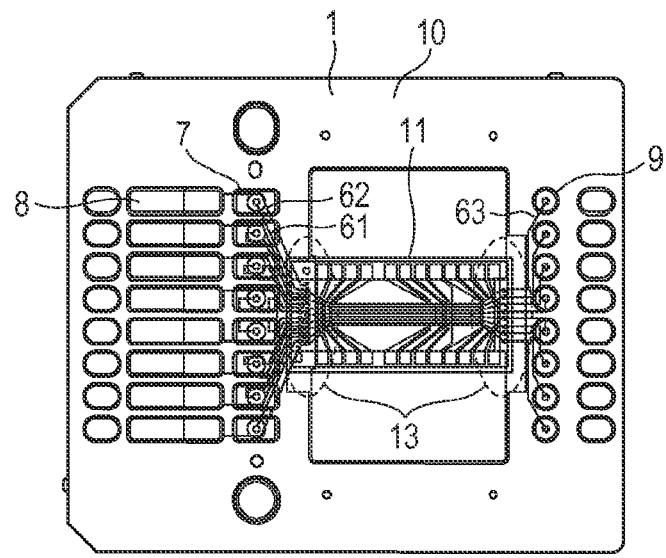
FIGS. 2A, 2B and 2C are views illustrating a device for analysis according to the embodiments of the present invention.
Figure 2B:
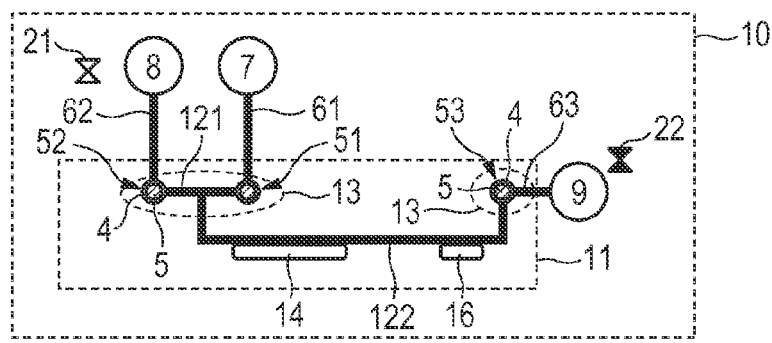
Figure 2C:
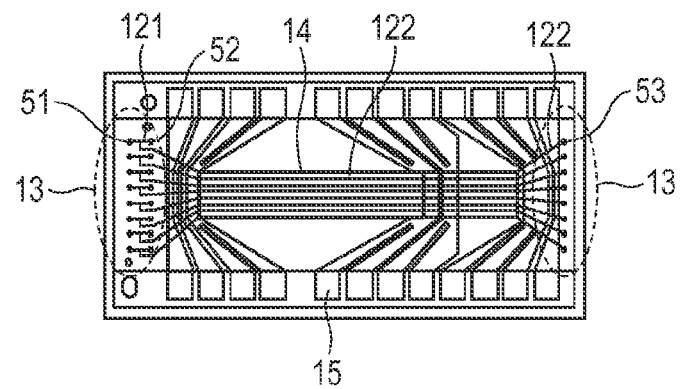

FIGS. 2A to 2C illustrate a device 10 for analysis in which a micro flow-channel chip (first chip) according to the present invention and a chip made from glass (second chip), which is a second micro flow-channel chip 11, are combined with each other. FIG. 2A is a top plan view of the device for analysis in which the micro flow-channel chip (first chip) according to the present invention and the chip made from glass (second chip), which is the second micro flow-channel chip, are combined with each other. FIG. 2B is a view illustrating a flow of a specimen in the device 10 for analysis. FIG. 2C is an enlarged view of a second micro flow-channel chip (second chip) 11. In FIG. 2B, one flow out of specimens flowing in a plurality of independent micro flow-channels is illustrated in order to simplify the description. In the figure, a specimen introduction portion 7 for introducing a specimen into a first micro flow-channel chip (first chip) is shown. In the figure, a first specimen discharge portion 8 of the first chip 1 and a second specimen discharge portion 9 of the first chip 1 are shown. A first flow channel 61 of the first chip 1, a second flow channel 62 of the first chip 1, and a third flow channel 63 of the first chip 1 are shown. A first flow-channel connection portion 51 of the first chip 1, a second flow-channel connection portion 52 of the first chip 1, and a third flow-channel connection portion 53 of the first chip 1 are shown. A first flow channel 121 of the second chip, and a second flow channel 122 of the second chip are shown. A portion 13 to be connected to the first chip, a heating unit 14 (heater for heating), a wiring portion 15 of the heater for heating, and a measuring portion 16 are shown. In addition, in the figure, a first micropump 21 provided on the first specimen discharge portion, and a second micropump 22 provided on the second specimen discharge portion are shown. The sending state of a specimen liquid is controlled by these micropumps.

The specimen introduction portion 7 is connected to the first flow channel 61 of the first chip. The first flow channel 61 of the first chip is connected to the first flow-channel connection portion 51. The flow-channel connection portion 51 is connected to the first flow channel 121 of the second chip. The first flow channel 121 of the second chip is connected to the second flow-channel connection portion 52 of the first chip. The second flow-channel connection portion 52 of the first chip is connected to the second flow channel 62 of the first chip. The first micropump 21 is connected to the second flow channel 62, and the micro flow-channel chip is configured so that the specimen is discharged to the first specimen discharge portion. In the present embodiment, a flow channel which is formed of a first flow channel 61 of the first chip, a flow-channel connection portion 51, a first flow channel 121 of the second chip, a second flow-channel connection portion 52 of the first chip and a second flow channel 62 is referred to as a specimen introduction preparation flow channel.

In addition, the first flow channel 121 of the second chip is connected to the second flow channel 122 of the second chip. In the present embodiment, the second flow channel 122 of the second chip is referred to as a specimen analysis flow channel.

Furthermore, the second flow channel 122 of the second chip is connected to a third flow-channel connection portion 53. The third flow-channel connection portion 53 is connected to a third flow channel 63 of the first chip 1. The second micropump 22 is connected to the third flow channel 63 of the first chip 1, and the micro flow-channel chip is configured so that the inspected specimen is discharged from the second specimen discharge portion 9 of the first chip. In the present embodiment, a flow channel is referred to as a specimen discharge flow channel, which is formed of the third flow-channel connection portion 53 of the first chip 1 and the third flow channel 63 of the first chip 1.

The specimen is introduced from the specimen introduction portion 7 by a not-shown syringe or the like. The specimen introduction preparation flow channel is filled with the specimen from the first specimen discharge portion 8, by the first micropump 21. After that, the specimen is guided to the second flow channel 122 (specimen analysis flow channel) of the second chip from the first flow channel 121 of the second chip, by the second micropump 22 from the second specimen discharge portion 9 of the first chip. Then, the specimen in the flow channel 122 is heated by a heating unit (heater) 14 arranged in the vicinity of the second flow channel 122 of the second chip. Platinum can be used for the heater which generates heat, and then can also detect the temperature from the resistance value. After that, the quantity of the fluorescence of the specimen is measured in the measuring portion 16 with the use of a CCD or CMOS sensor or the like. Then, the measured specimen is discharged from the second specimen discharge portion 9 of the first chip from the third flow-channel connection portion 53 of the first chip 1 through the third flow channel 63 of the first chip 1.

Incidentally, the specimen introduction portion 7 may be manufactured into an integrated shape with the micro flow-channel chip 1 by die molding, or may be used in a form of being bonded to the micro flow-channel chip 1 as another component.

Figure 3A:
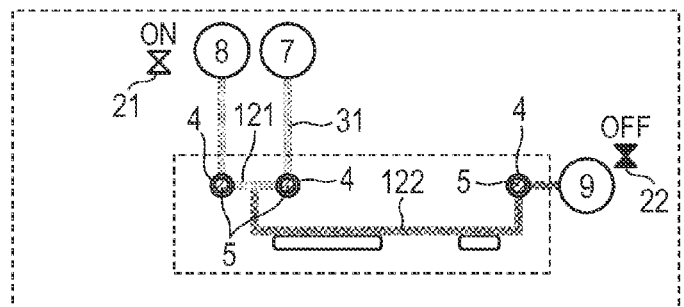
FIGS. 3A, 3B, 3C, 3D and 3E are views illustrating a method of using the device for analysis.
Figure 3B:
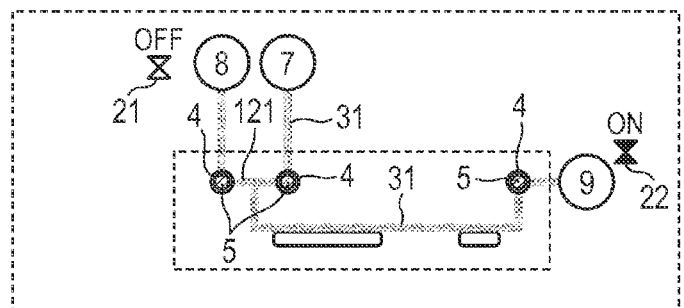
Figure 3C:
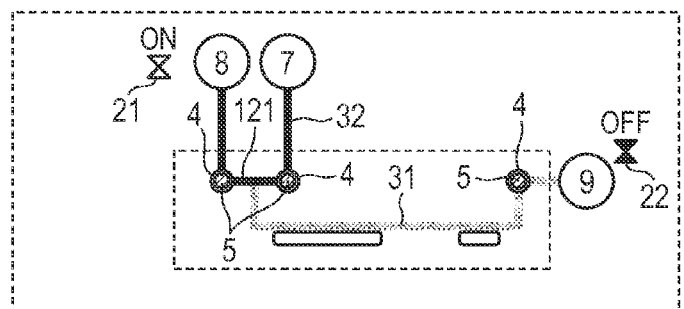
Figure 3D:
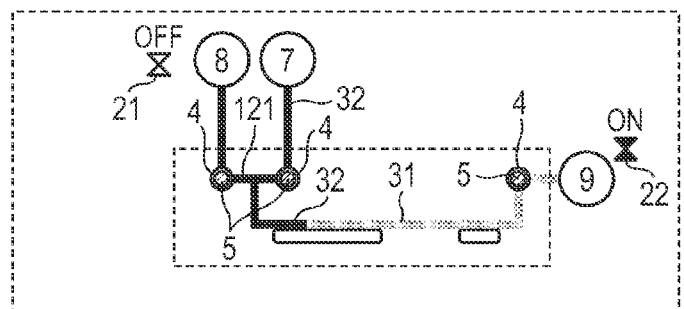
Figure 3E:
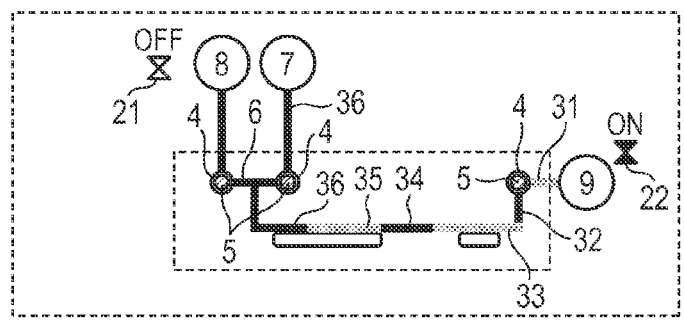

Next, the introduction of the specimen will be described with reference to FIGS. 3A to 3E. FIGS. 3A to 3E illustrate an example in which plural kinds of specimens are continuously introduced into a specimen analysis flow channel (flow channel 122 of second chip), based on the device for analysis described in FIGS. 2A to 2C. Portions having the same functions as those in FIGS. 2A to 2C are designated by the same reference numerals, and the description will be omitted. FIG. 3A is a view illustrating a first form in which a first specimen is guided to the specimen introduction preparation flow channel. FIG. 3B is a view illustrating a second form in which the first specimen is guided to the specimen analysis flow channel from the specimen introduction preparation flow channel. FIG. 3C is a view illustrating a third form in which a second specimen is guided to the specimen introduction preparation flow channel. FIG. 3D is a view illustrating a fourth form in which the second specimen is guided to the specimen analysis flow channel from the specimen introduction preparation flow channel. FIG. 3E is a view illustrating the state in which several kinds of specimens have been guided to the device for analysis (specimen analysis flow channel). In the figure, a first specimen 31, a second specimen 32, a third specimen 33, a fourth specimen 34, a fifth specimen 35 and a sixth specimen 36 are shown.

Firstly, the first micropump 21 is turned ON, and the second micropump 22 is turned OFF. While the first specimen 31 is added dropwise to the flow channel 61 as a droplet from the specimen introduction portion 7 by a not-shown syringe or the like, the first specimen 31 is sucked by the first micropump 21, and the specimen introduction preparation flow channel is filled with the first specimen 31 (*a*).

Next, the first micropump 21 is turned OFF, and the second micropump 22 is turned ON. Then, while the first specimen 31 in an amount sufficient to fill up the flow channel is subsequently added dropwise to the specimen introduction portion 7, the first specimen 31 is sucked from the specimen discharge portion 9 by the second micropump 22. Thereby, the first specimen 31 which fills the inside of the specimen introduction preparation flow channel is guided to the specimen analysis flow channel 122 (*b*). Also after the specimen analysis flow channel (flow channel 122 of second chip) has been filled with the first specimen 31, air bubbles or the like are not mixed thereinto because the specimen introduction portion is filled with the first specimen up to the inlet or to the vicinity of the inlet.

Next, the first micropump 21 is turned ON, and the second micropump 22 is turned OFF. Then, the second specimen 32 is introduced into the specimen introduction portion. At this time, the specimen introduction portion is filled with the first specimen 31, and accordingly the first specimen 31 and the introduced second specimen 32 are integrated due to surface tension. At this time, even if air bubbles are generated, the air bubbles are exhausted from an aperture in the top face of the specimen introduction portion by the surface tension (c). While the second specimen 32 is added dropwise to the specimen introduction portion, the second specimen 32 is sucked by the first micropump 21. Thereby, the first specimen 31 is all discharged to the specimen discharge portion 8, and the specimen introduction preparation flow channel is filled with the second specimen 32 (a).

Next, the first micropump 21 is turned OFF, and the second micropump 22 is turned ON. Then, while the second specimen 32 is subsequently added dropwise to the specimen introduction portion 7, only a predetermined amount of the second specimen 32 is sucked by the second micropump 22. Thereby, the predetermined amount of the second specimen 32 which fills the specimen introduction preparation flow channel is introduced into the specimen analysis flow channel (flow channel 122 of second chip) (d). The operations are repeated, and thereby the predetermined amounts of a plurality of specimens (32 to 36) are respectively introduced sequentially into the specimen analysis flow channel (flow channel 122 of second chip) (e).

Here, a fixed time period is needed before the second specimen 32 is introduced and the specimen introduction preparation flow channel is filled again with the second specimen 32, after the state in which the specimen introduction preparation flow channel is filled with the first specimen 31 in the above described step. If the first specimen 31 remains after the specimen has been changed to the second specimen, a specimen in which the first specimen 31 and the second specimen 32 are mixed results in being introduced into the specimen analysis flow channel (flow channel 122 of second chip), which causes an analysis failure. In order to eliminate this failure, the first specimen must be discharged completely from the specimen introduction preparation flow channel, when the specimens are changed.

In order to shorten this time period for the change, make the first specimen resist remaining in the specimen introduction preparation flow channel and perform an efficient analysis, it is effective to reduce a difference of a cross-sectional area (cross-sectional area perpendicular to longitudinal direction of flow channel) or a volumetric capacity (cross-sectional area×length of flow channel), in the specimen introduction preparation flow channel. Thereby, the specimen can be prevented from being detained. The detention tends to easily occur particularly in the flow-channel connection portions 51 and 52. It is effective for suppressing the detention of the specimen to reduce a difference between the cross-sectional areas of the first flow channel 61 and the second flow channel 62 and the cross-sectional areas of the holes of the first flow-channel connection portion 51 and the second flow-channel connection portion 52. In addition, it enables an inspection with a smaller amount of specimen to decrease the volumetric capacity of the specimen introduction preparation flow channel, and enables efficient analysis.

Here, an example has been described in which the first specimen 31 is introduced and then the second specimen 32 is introduced, but a buffer solution which prevents the mixing of the first specimen 31 and the second specimen 32 and functions as a spacer may be introduced between the first specimen 31 and the second specimen 32. The buffer solution can be introduced with the same method as in the case of the second specimen 32. In addition, similarly, the buffer solution which functions as the spacer may be introduced between each specimen of a plurality of specimens (between second specimen 32 and third specimen, between third specimen 34 and fourth specimen 35, and so on).

The micro flow-channel chip according to the present invention has the projecting portion provided in the inner part of the through hole which exists at least in one part that constitutes the micro flow-channel chip, thereby reduces a volumetric capacity of the flow channel, and can reduce the amount of the specimen to be used. Accordingly, a time period can be reduced which is spent before the next introduced specimen lets the remaining previous specimen flow out, and the efficient analysis can be performed.

EXEMPLARY EMBODIMENT

FIGS. 1A to 1F illustrate a configuration of an exemplary embodiment of a micro flow-channel chip according to the present invention.

In the figure, a bore diameter φ in the portion is shown which is connected to a first flow channel 121 of a chip made from glass that is a second micro flow-channel chip in the micro flow-channel chip, and a height h of the hole is shown. In addition, in the figure, a width a of a groove 611 which constitutes a flow channel 61 is shown, and a depth b of the flow channel 61 is shown.

In the present exemplary embodiment, a bore diameter of a through hole 4 was set at φ0.35 mm, and a height h thereof was set at 1 mm. When a first part 2 was manufactured, a die having such a shape that the shape of the part was inverted was manufactured, and the first part 2 was manufactured with the die molding. In addition, when the first part 2 was manufactured by die molding, an extraction gradient of 2 degrees was given to the through hole 4 so that the first part 2 was not deformed when having been released from the die. The portion on the die corresponding to the through hole 4 having φ0.35 mm was formed by a pin on the die having φ0.35 mm.

As for the shape of the flow channel 61 in the second part 3, a width a of a groove 1 was set at 0.10 mm, and a depth b was set at 0.05 mm. In addition, a projecting portion 5 which fitted in the inner part of the through hole 4 when the second part 3 is bonded to the first part was formed into such a circular truncated cone shape with φ0.25 mm and a gradient of 2 degrees. In addition, the height of the projecting portion 5 was set at 1 mm which was the same as the height h of the hole. When the second part was manufactured, a die having such a shape that the shape of the part was inverted was manufactured, and the second part was manufactured with the die molding. After that, the first part 2 and the second part 3 were bonded to each other with an ultraviolet-curable type adhesive, and thereby the micro flow-channel chip 1 according to the present invention was obtained. The obtained micro flow-channel chip 1 had the projecting portion provided in the inner part of the through hole, thereby had a reduced volume of the flow-channel connection portion 51, could have a configuration in which the previous specimen resisted remaining in the chip when the specimen was changed, and besides, could reduce the amount of the specimen to be used. As a result, efficient analysis could be performed.

Here, if the through hole to be connected to the second micro flow-channel chip of the first part 2 is formed so as to have a bore diameter φ of φ0.18 mm, a flow channel having a volumetric capacity equivalent to that in the above described configuration in the present invention is obtained without having no projection shape. However, in a case where the through hole having φ0.18 mm is manufactured by die molding, the pin on the die, which is used for forming the through hole of the first part, must also be set at φ0.18 mm. As a result, the damage of the pin is caused by a pressure of a resin in the die molding and/or a resistance occurring when the resin is released from the die, and thereby it becomes difficult to stably mold the through hole by the die molding.

In the micro flow-channel chip of the present invention, the projecting portion which the second part has is inserted into the through hole of the first part that forms the flow-channel connection portion 51, and thereby the volume of the flow-channel connection portion 51 is reduced, in other words, the sectional area in the flow-channel connection portion 51 is reduced. Thereby, the micro flow-channel chip has obtained such a configuration that the specimens resist being mixed when the specimens are changed. Accordingly, the accuracy of analysis increases, also an operation of letting the remaining previous specimen flow out by a specimen to be introduced next becomes unnecessary, and the effective analysis can be performed. In addition, the first part and the second part of the micro flow-channel chip of the present invention can be manufactured by die molding, and accordingly the cost of the manufacture can be reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-221096, filed Oct. 24, 2013, which is hereby incorporated by reference herein in its entirety.

What is claimed is:

1. A micro flow-channel chip formed of two or more parts, wherein a first part has a through hole that forms a flow-channel connection portion which is connected to a micro flow-channel formed on the surface of a second part, the second part comprising a projecting portion, and the projecting portion of the second part is inserted into an inner part of the through hole of the first part, thereby reducing a volume of the flow-channel connection portion.

2. The micro flow-channel chip according to claim 1, wherein the first part includes a cycloolefin polymer, polymethyl methacrylate, polycarbonate, a methyl methacrylate styrene copolymer or polystyrene.

3. The micro flow-channel chip according to claim 1, wherein the second part includes a cycloolefin polymer, polymethyl methacrylate, polycarbonate, a methyl methacrylate styrene copolymer or polystyrene.

4. The micro flow-channel chip according to claim 1, wherein the through hole has an inclined inner wall, and an angle of the inclination of the inner wall is 1 degree or more and 5 degrees or less.

5. The micro flow-channel chip according to claim 1, wherein the projecting portion has a shape of a circular truncated cone shape, a conical shape, a polygonal pyramid shape or a polygonal truncated pyramid shape.

6. The micro flow-channel chip according to claim 5, wherein the projecting portion has the shape of the circular truncated cone shape, and an angle of the inclination of a slope of the circular truncated cone shape is 1 degree or more and 5 degrees or less.

7. The micro flow-channel chip according to claim 1, wherein both of the first part and the second part are molded with a die.

8. A micro flow-channel device having the micro flow-channel chip according to claim 1.

9. A device for analysis, comprising: a first micro flow-channel chip formed of two or more parts, wherein a first part has a through hole that forms a flow-channel connection portion which is connected to a micro flow-channel, a second part comprising a projecting portion, and the projecting portion of the second part is inserted into an inner part of the through hole of the first part, thereby reducing a volume of the flow-channel connection portion; and a second micro flow-channel chip having a micro flow-channel formed therein which is connected to the flow-channel connection portion.

10. The device for analysis according to claim 9, wherein the second micro flow-channel chip has a specimen analysis flow channel connected to the micro flow-channel.

11. The device for analysis according to claim 9, wherein the second micro flow-channel chip is a micro flow-channel chip made from glass.

12. The device for analysis according to claim 9, wherein the second micro flow-channel chip has a heating unit and a measuring portion.

13. A method for manufacturing a micro flow-channel chip which is formed of two or more parts, comprising:
    manufacturing a first part having a through hole with die molding, by using a first die;
    manufacturing a second part having a projecting portion with die molding, by using a second die; and
    joining the first part with the second part, wherein the projecting portion is inserted into an inner part of the through hole to form a flow-channel connection portion, thereby reducing a volume of the flow-channel connection portion.

14. The method for manufacturing the micro flow-channel chip according to claim 13, wherein the parts are joined with each other by thermo compression bonding, bonding by an adhesive, threading or sandwiching.

15. The method for manufacturing the micro flow-channel chip according to claim 13, wherein at least one of the first part and the second part includes a cycloolefin polymer, polymethyl methacrylate, polycarbonate, a methyl methacrylate styrene copolymer or polystyrene.

* * * * *